United States Patent
Gu et al.

(10) Patent No.: US 9,492,589 B2
(45) Date of Patent: Nov. 15, 2016

(54) PREPARATION OF EXTRACELLULAR MATRIX-MODIFIED TISSUE ENGINEERED NERVE GRAFTS FOR PERIPHERAL NERVE INJURY REPAIR

(71) Applicant: NANTONG UNIVERSITY, Nantong, Jiangsu (CN)

(72) Inventors: Xiaosong Gu, Jiangsu (CN); Fei Ding, Jiangsu (CN); Yun Gu, Jiangsu (CN); Chengbin Xue, Jiangsu (CN); Yumin Yang, Jiangsu (CN); Yongjun Wang, Jiangsu (CN); Leilei Gong, Jiangsu (CN)

(73) Assignee: NANTONG UNIVERSITY (CN)

( * ) Notice: Subject to any disclaimer, the term of this patent is extended or adjusted under 35 U.S.C. 154(b) by 0 days.

(21) Appl. No.: 14/762,243

(22) PCT Filed: May 27, 2013

(86) PCT No.: PCT/CN2013/076239
§ 371 (c)(1),
(2) Date: Jul. 21, 2015

(87) PCT Pub. No.: WO2014/114043
PCT Pub. Date: Jul. 31, 2014

(65) Prior Publication Data
US 2015/0352255 A1 Dec. 10, 2015

(30) Foreign Application Priority Data
Jan. 25, 2013 (CN) .......................... 2013 1 0028903

(51) Int. Cl.
| | |
|---|---|
| *A61L 27/36* | (2006.01) |
| *A61L 27/54* | (2006.01) |
| *A61L 27/38* | (2006.01) |
| *A61L 27/22* | (2006.01) |
| *A61L 27/24* | (2006.01) |
| *A61L 27/20* | (2006.01) |
| *A61L 27/18* | (2006.01) |
| *C12N 5/00* | (2006.01) |

(52) U.S. Cl.
CPC ............ *A61L 27/3675* (2013.01); *A61L 27/18* (2013.01); *A61L 27/20* (2013.01); *A61L 27/227* (2013.01); *A61L 27/24* (2013.01); *A61L 27/3604* (2013.01); *A61L 27/3683* (2013.01); *A61L 27/3687* (2013.01); *A61L 27/3878* (2013.01); *A61L 27/3895* (2013.01); *C12N 5/0062* (2013.01); *A61L 2430/32* (2013.01); *C12N 2513/00* (2013.01); *C12N 2525/00* (2013.01); *C12N 2527/00* (2013.01)

(58) Field of Classification Search
None
See application file for complete search history.

(56) References Cited

U.S. PATENT DOCUMENTS

| | | | | |
|---|---|---|---|---|
| 6,962,814 | B2 * | 11/2005 | Mitchell | ............. A61L 27/3691 424/93.1 |
| 7,402,319 | B2 * | 7/2008 | Schmidt | ............. A61L 27/3604 424/422 |
| 2011/0143429 | A1 * | 6/2011 | Chun | ...................... A61L 27/18 435/325 |

FOREIGN PATENT DOCUMENTS

| | | |
|---|---|---|
| CN | 1589913 A | 3/2005 |
| CN | 101434934 A | 5/2009 |
| CN | 101616698 A | 12/2009 |
| CN | 102343114 A | 2/2012 |
| CN | 103041450 A | 4/2013 |
| WO | 2005046457 A2 | 5/2005 |
| WO | 2011119804 A2 | 9/2011 |
| WO | 2012094611 A1 | 7/2012 |

OTHER PUBLICATIONS

Application No. PCT/CN2013/076239, International Search Report dated Nov. 7, 2013. 4 pages.
Application No. PCT/CN2013/076239, International Search Report and the Written Opinion of the International Searching Authority dated Nov. 7, 2013. 12 pages, Jul. 13, 2016.

\* cited by examiner

*Primary Examiner* — Allison Fox
(74) *Attorney, Agent, or Firm* — Schmeiser, Olsen & Watts, LLP (57) ABSTRACT

A tissue engineered nerve graft for repairing peripheral nerve injury consists of a nerve conduit and a extracellular matrix (ECM) that is secreted by autologous or allogeneic support cells and obtained by decellularization. A preparation method of the ECM-modified tissue engineered nerve grafts containing support cells, nerve conduit and constructing a ECM-modified tissue engineered nerve graft.

14 Claims, 9 Drawing Sheets

PREPARATION OF EXTRACELLULAR MATRIX-MODIFIED TISSUE ENGINEERED NERVE GRAFTS FOR PERIPHERAL NERVE INJURY REPAIR

CROSS-REFERENCE TO RELATED APPLICATIONS

This application claims priority to PCT Application No. PCT/CN2013/076239, having a filing date of May 27, 2013, based on CN 201310028903.6 having a filing date of Jan. 25, 2013, the entire contents of which are hereby incorporated by reference.

FIELD OF TECHNOLOGY

The following is in the technical field of medical biomaterials used for transplants into the human body, refers to the preparation of extracellular matrix (ECM)-modified tissue engineered nerve grafts for peripheral nerve injury repair

BACKGROUND

With the progress of social modernization and the pace acceleration of people's daily life, an increasing number of accidents, resulting from traffic, industry, and sports, local wars, violent events, and natural disasters (e.g. earthquakes), will lead to peripheral nerve injury. When the formed nerve defect of middle and long distance cannot be treated by end-to-end suture in the clinic, peripheral nerve grafting has to be applied to bridge the nerve defect. Although nerve grafts have been searched for and developed for more than a hundred years, great efforts are still devoted to the development of ideal nerve grafts to substitute autologous nerve grafts in clinical practice. Despite being a golden standard for peripheral nerve repair, autologous nerve grafting can not be widely used in the clinic due to its several limitations, such as deficient supply of donor nerves, mismatch between the injured nerve and the donor nerve in the structure and size, as well as donor site morbidity and secondary deformities.

The emergence and advance of the tissue engineering field provide a unique opportunity to generate a tissue engineered nerve grafts as a promising alternative to autologous nerve grafts. The existing tissue engineered grafts mainly include two important types. One type is the acellular allogeneic nerve, i.e. acellular nerve graft (ANG), in which the cells in the allogeneic tissue are removed but the original neural architecture was kept. The ANG meets the basic requirements for nerve grafts in peripheral nerve tissue engineering, and becomes aft tissue-derived ECM modified tissue engineered nerve grafts. For example, a research article has indicated that ANG induces differentiation of adult rat BMSCs into Schwann cells (He Hongyun, Deng Yihao, Ke Xiaojie, et al, *Morphologic Study of Bone Marrow Stromal Cells of Rat Differentiating into Schwann Cells By Acellularnerve Grafts. Chinese Journal of Neuroanatomy,* 2007; 23(6):). Another study investigates the protective effects of the implanted ANG on motor neurons of the anterior horn of the spinal cord (Liu Jinchao, Lin Xiaoping, Ke Xiaojie, et al. *The Protective Effects of Acellularnerve Matrix Allografts on the Motor Neurons of the Anterior Horn of Spinal Cord Progress of Anatomical Sciences,* 2005(3): 206-209), and indicates that the use of ANGs to bridge peripheral nerve defects has had excellent protective effects on the survival of the cell body of motor neurons. Although there are a large number of studies on the preparation technology of ANGs achieving the faster progress, many preparation methods have complicated procedures, and the fine structure and mechanical properties of biomaterials will be impacted during processing.

Another type is based on a nerve conduit prepared with a proper mould and having ECM or support cells coated on its inner and outer surfaces. For example, a research article reports on the use of a bridge graft made up of olfactory ensheathing cells (OECs)-Schwann cells (SCs) derived ECM and poly(DLlactide-co-glycolide acid) (PLGA) to protect the peripheral target organs and spinal cord neurons after sciatic nerve injury (You Hua, Jiao Shusheng, Feng Shuainan, et al, *The Protective Effects of Tissue Engineering Artificial Nerves on Peripheral Target Organs and Spinal Cord Neurons after Sciatic Nerve Defect Chinese Journal of Trauma,* 2010 Vol. 26 No. 3 P. 265-269) As another example, a Chinese patent (an application No. of CN03134541.7 and an application publication No of CN1589913) entitled "A tissue engineering peripheral nerve used for repairing peripheral nerve defect and its preparation method" describes a tissue engineered nerve used for repairing peripheral nerve defect. The tissue engineered nerve consists of a nerve conduit made of biodegradable materials added with glial cells or stem cells having ability to differentiate into glial cells, which are used as seed cells, and modified with microspheres for controlled release of neurotrophic factors and with ECM molecules.

At present, support cells used in the tissue engineered nerves include Schwann cells and various stem cells, which are allogeneic cells, and may cause immunogenicity, which is not suitable for clinic applications. On the other hand, the in vivo fate and biological effects of support cells after they are implanted into the body are not fully clear, and they may be inactivated in the environment of the body, thus failing to achieve expected biological effects. All the above issues limit the development of tissue engineered nerve grafts.

SUMMARY

An aspect relates to engineered cell-derived ECM modified tissue engineered nerve grafts for repairing peripheral nerve injury. The nerve grafts are beneficial to cell adhesion, and likely to prompt axonal regeneration, thus overcoming the drawbacks of existing technologies. The following is based on tissue engineering methods, and adopts a rotational cell reactor to culture support cells in a nerve conduit and luminal filaments, and then applies decellularization to stimulate ECM secretion from support cells, thus generating the support cells-derived ECM modified tissue engineered nerve grafts for peripheral nerve injury repair. The following may overcome limitations of autologous nerve grafting, avoid the immunogenicity of allogeneic nerve grafts, provide ECM beneficial to neural cell adhesion, and establish an environment suitable for axonal regrowth. Therefore, the following helps to promote nerve regeneration and function restoration, and will be developed into a feasible clinical therapy.

The technical scheme is as follows:

A tissue engineered nerve graft for repairing peripheral nerve injury consists of a nerve conduit and a ECM that is secreted by autologous or allogeneic support cells and obtained by decellularization. The support cells can be either one alone or a combination of Schwann cells, skin-derived fibroblastes, skin stem cells, bone marrow mesenchymal stem cells or induced pluripotent stem cells. The nerve conduit is made of biodegradable materials, and is preferably made up of either one alone or a combination of of silk fibroin, chitosan, collagen, polylactic acid or polyglycolic acid.

The nerve conduit may be simply a tissue engineered nerve graft usually prepared and used in the field. A surface-porous chitosan-based nerve conduit is preferable, which has a porosity of 50-90%, a pore size of 50-300 μm, high tensile strength, the inside diameter of 0.5-8 mm, and the wall thickness of 0.1-3 mm, and can be prepared with reference to the method described in the patent (application No. CN201110324474.8, entitled "Tissue Engineering Nerve Graft and Its Functions". Another silk fibroin-based nanoscale nerve conduit is also preferable, which can be prepared specifically with reference to the method described in the patent (application No. CN200910034583.9 and publication No. CN101664346, entitled "Artificial Nerve Graft Prepared by Electrospinning, Its Preparation Method, and Related Devices". The third nerve conduit of choice has a composite structure, which consists of a surface-porous chitosan-based nerve conduit or silk fibroin-based nerve conduit (either nerve conduit can be prepared by referring the above patents) with introduction of 120 silk fibroin filaments as luminal fillers.

Embodiments of the present invention also provides a preparation method of the tissue engineered nerve graft modified by a natural cell matrix for repairing peripheral nerve defects, which prepares a tissue engineered nerve graft containing support cells and then decellularizes to obtain a decellularized tissue engineered nerve graft. The support cells-containing tissue engineered nerve graft may be prepared through a cell culture to make support cells adhered on the inner and outer surface of a nerve conduit, where a three-dimensional microgravity cell culture method is preferred. Embodiments of the present invention uses a RCMW type Synthecon microgravity three-dimensional culture system.

The preferred technical scheme for the preparation of support cells-containing tissue engineered nerve nerve grafts and decellularized grafts are as follows:

(1) Preparation of support cells-containing tissue engineered nerve nerve grafts. A 100 ml complete medium is slowly put to a culture vessel, and then $2.5 \times 10^7$ cells and a sterile nerve conduit are added, followed by processing with a peristaltic pump to ensure the final cell density of $1 \times 10^5$/ml. After air is exhausted from the culture vessel, a rotational microgravity circulation perfusion culture is initiated with a rotational bioreactor placed in a 37° C. $CO_2$ incubator to ensure a full contact and adhesion of cells onto the nerve conduit by setting the rotating speed of 10 r/min at the first 24 h, and then to make the nerve conduit suspended in a culture solution by adjusting the rotating speed after 24 h. Following culture for 2 d, the medium is changed with a differentiation medium to promote ECM secretion, and allowed to culture for two more weeks before the nerve conduit coated with support cells is taken out. The optimized composition of the differentiation medium is H-DMEM+ 15% FBS+50 ng/ml HRG+2 μm forsklin+50 μg/ml Vc.

(2) Preparation of ECM-modified tissue engineered nerve grafts. The support cell-containing tissue engineered nerve graft is subjected to decellularization. It is washed with phosphate buffered saline (PBS), placed in sterile deionized water at 37° C. for hypotonic treatment for 10 min, followed by cell lysis in a nonionic detergent for 10-15 min at 37° C., and then added in a nonionic detergent added with Dnase I (4 mg/ml) for 30 min digestion at 37° C. to remove DNA. The acellular product is kept at −80° C. for use. The optimized composition of the nonionic detergent is phosphate buffered saline consisting of 0.5% TritonX-100 and 20 mM aqueous ammonia.

The support cells used in the above procedures are either one alone or a combination of Schwann cells, skin-derived fibroblastes, skin stem cells, bone marrow mesenchymal stem cells and induced pluripotent stem cells, while the nerve conduit is made up of biodegradable materials, which are either one alone or a combination of silk fibroin, chitosan, collagen, polylactic acid and polyglycolic acid. A surface-porous chitosan-based nerve conduit is preferable, which has a porosity of 50-90%, a pore size of 50-300 μm, high tensile strength, the inside diameter of 0.5-8 mm, and the wall thickness of 0.1-3 mm, and can be prepared with reference to the method described in the patent (application No. CN201110324474.8 entitled "Tissue Engineering Nerve Graft and Its Functions". Another silk fibroin-based nanoscale nerve conduit is also preferable, which can be prepared specifically with reference to the method described in the patent (application No. CN200910034583.9 and publication No. CN101664346 entitled "Artificial Nerve Graft Prepared by Electrospinning, Its Preparation Method, and Related Devices". The third nerve conduit of choice has a composite structure, which consists of a surface-porous chitosan-based nerve conduit or silk fibroin-based nerve conduit (either nerve conduit can be prepared by referring the above patents) with an introduction of 120 silk fibroin filaments as luminal fillers.

Embodiments the present invention have the following advantages:

(1) The ECM is generally composed of collagen (Col), laminin (LN), fibronectin (FN), hyaluronic acid, and proteoglycan (such as chondroitin sulfate, heparan sulfate proteoglycan). ECM provides mechanical support and physical strength for the integrity of tissues, organs, and the whole organism. Evidence shows that LN, FN and Col can provide suitable "adhesiveness" for nerve growth, make axons grow along a matrix bridge, and guide the directional growth of nerve fibers. One or more ECM components, such as LN and FN, have been mostly adopted in the current field of tissue engineering. The commercially available, synthesized ECM, however, are expensive and their components are relatively single. The natural, cell-derived ECM, obtained in embodiments of the present invention after decellularization of cultured cells, can keep various important components and framework of ECM, and is more beneficial to the adhesion of nerve cells, and has a certain guiding effect on oriented axonal regeneration, thus promoting nerve regeneration. Moreover, it has the cheaper price than an synthesized ECM, and is easier to be accepted by patients.

(2) Support cells used in tissue engineered nerve grafts include Schwann cells and various stem cells. Most of these cells are allogeneic cells, which may cause immunogenicity during implantation. The ECM contained in tissue engineered nerve grafts developed in embodiments of the present invention is obtained after decellularizing cultured cells, thus leading to less or no immunogenicity. The tissue engineered nerve grafts are suitable for a large population of users.

(3) Tissue engineered nerve grafts developed by embodiments of the present invention are prepared by a three-dimensional microgravity cell culture method, which enables support cells to be uniformly adhered to the inner and outer surfaces of luminal filaments, and the ECM obtained after decellularization is also uniformly distributed on the inner and outer surfaces of luminal filaments, thus facilitating nerve regeneration.

(4) Tissue engineered nerve grafts developed in embodiments of the present invention contain no exogenic toxic substances, which may be probably introduced during preparation process, and also have excellent biocompatibility and biodegradability, as well as good mechanical property. The wall of nerve conduits exhibits a 3-D microporous structure, which facilitates transportation of nutrients required by nerve growth. The silk fibroin filaments included in the conduit lumen are prepared by electrostatic spinning, having a large specific surface area to serve as a required space for the growth of nerve cells.

BRIEF DESCRIPTION

Some of the embodiments will be described in detail, with reference to the following figures, wherein like designations denote like members, wherein:

FIG. 1 (A) Light micrograph of Schwann cells.

FIG. 1 (B) Immunohistochemistry micrograph of Schwann cells, which are immunopositive to S100 (grey spindle-like) with nuclei labeled by Hoechst33342 (grey point).

FIG. 2 (A) Light micrograph of fiberblasts (100×).

FIG. 2 (B) Immunohistochemistry micrograph of fiberblasts (100×), which are immunopositive to their marker (grey) with nuclei labeled by Hoechst33342 (white).

FIG. 3 (A) Light micrograph of skin stem cells (100×).

FIG. 3 (B) Immunohistochemistry micrograph of skin stem cell spheres (100×), which are immunopositive to Versican (a) and Nestin (b) with nuclei labeled by Hoechst33342 (c), and (d) is the merge of (a), (b), and (c).

FIG. 3 (C) Immunohistochemistry micrograph of skin stem cell spheres (100×), which are immunopositive to Vimentin (a) and Nestin (b) with nuclei labeled by Hoechst33342 (c), and (d) is the merge of (a), (b), and (c).

FIG. 4 (A) Shows induced differentiation of skin stem cells into a Schwann cells. Light micrograph (100×).

FIG. 4 (B) Shows local magnification of Schwann cell colonies that are formed by induced differentiation of skin stem cells.

FIG. 5 (A) Immunohistochemistry micrograph of Schwann cells formed by induced differentiation of skin stem cells (100×). The differentiated Schwann cells are immunopositive to S100.

FIG. 5 (B) An Immunohistochemistry micrograph with differentiated Schwann cells with nuclei labeled by Hoechst33342 (B).

FIG. 5 (C) is the merger of (A) and (B).

FIG. 7 (A) Immunochemistry micrograph of ECM. Light micrograph of ECM on the material surface after decellularization.

FIG. 7 (B) ECM is immunopositive to anti-FN.

FIG. 7 (C) ECM is immunopositive to anti-LN.

FIG. 7 (D) is the merger of (B) and (C).

FIG. 8 (A) Effects of ECM on neuronal growth. NF immunochemistry micrograph of neurons cultured on ECM, where an ECM group refers to neurons cultured on purchased ECM and an N-ECM group refers to neurons cultured on ECM obtained after decellularization of support cells.

FIG. 8 (B) Shows cell vitality of neurons.

FIG. 8 (C) Western blot images showing the expression of neural cell adhesion molecule (NCAM) and axon growth-associated protein (GAP43).

FIG. 9 (A) Scanning electron micrograph (SEM) of an ECM modified tissue engineered nerve graft. SEM of the inner surface of a support cells-containing nerve conduit. The support cells are uniformly distributed on the inner surface.

FIG. 9 (B) SEM of the inner surface of a nerve conduit treated by decellularization. ECM is generated and visible.

FIG. 9 (C) SEM of silk fibroin filaments within the lumen of a support cells-containing nerve conduit.

FIG. 9 (D) SEM of silk fibroin filaments within the lumen of a nerve conduit treated by decellularization.

FIG. 10 (A) Immunochemistry micrograph of ECM on the surface of silk fibroin filaments within the lumen of a nerve conduit treated by decellularization. Shows Immunopositive to anti-FN.

FIG. 10 (B) Shows Immunopositive to anti-FN.

FIG. 10 (C) shows silk fibroin filaments.

FIG. 10 (D) is a merger of (A), (B), and (C).

FIG. 11 (A) An NF-labeled axonal regrowth (Scale bar, 200 μm) for a material group at one week post-grafting.

FIG. 11 (B) shows an ECM group at one week post-grafting.

FIG. 11 (C) shows an NF-labeled axonal regrowth (Scale bar, 200 μm) for a material group at 2 weeks post-grafting.

FIG. 11 (D) shows an ECM group at 2 weeks (D) post-grafting.

FIG. 13 (A) SEM micrograph of cross sectional regenerated nerve at the middle portion (Scale bar, 5 μm) for a material group and ECM group (B).

FIG. 13 (B) SEM micrograph of cross sectional regenerated nerve at the middle portion (Scale bar, 5 μm) for an ECM group.

DETAILS OF SCHEME

Unless defined otherwise, all terms used in embodiments of the present invention have the same meaning as commonly used by the researchers in the field of tissue engineering.

Embodiments of the present invention will be further described with reference to the working examples. The descriptions of these working examples are only used for illustration of the present invention, but not intended to limit the scope of the present invention in any manner.

In the following examples, various processes and methods which are not described in details are conventional methods known in the field of tissue engineering.

Working Example 1

Culture and Purification of Schwann Cells

Figure 1:
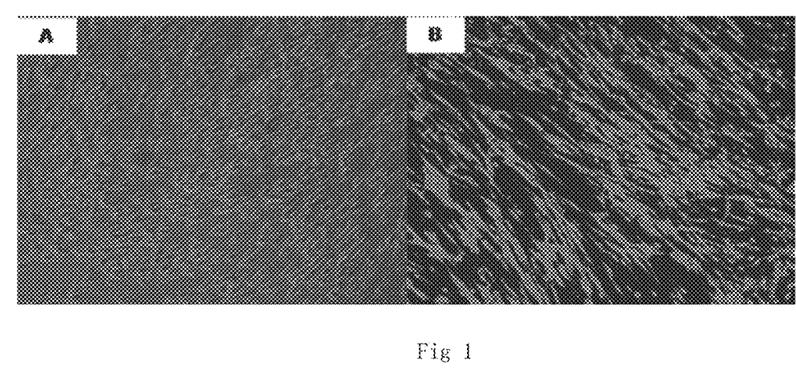

Newborn SD rats (1 day old) are killed and disinfected with alcohol. The sciatic nerve at the two sides are taken and placed in an ice-bath operating board to remove epineuriums and adhesions. After digestion with collagenase/pancreatin, centrifugation is conducted and a supernatant is abandoned. Then cells are resuspended through a complete medium and seeded to a PDL-coated culture dish for 24 h culture. Afterwards, a complete medium containing cytarabine (10 μM) is replaced for 48 h culture, and then a complete medium containing HRG (50 ng/ml) and Forsklin (2 μM) is replaced for continuous culture with the medium is changed every 3 d until cell fusion, followed by pancreatin digestion and centrifugation to obtain cell precipitates, which are resuspended using 1 ml complete medium containing Thy1.1 (1:1000) and to allow incubation on ice for 2 h. Centrifugation is conducted and a supernatant is abandoned. The cells are resuspended using a mixture of DMEM and complement (3:1), incubated for 1 h at 37° C., scavenged twice using the complete medium after centrifugation, and re-inoculated in the culture dish. The medium is changed every other day, and the cells can be used after growth to cover the container (the cell culture and identification are shown in FIGS. 1 A-B).

Working Example 2

Culture of Skin-Derived Fibroblastes

Figure 2:
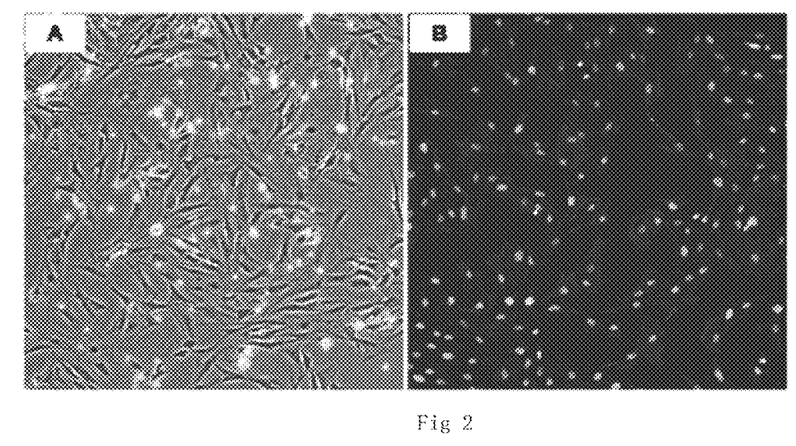

Newborn SD rats (1 day old) are killed and disinfected with alcohol Skins in the back are taken out and placed in a pre-cooled dissection solution to remove subcutaneous tissue (fat, hypodermic fascia layer, and blood vessels). After wash thrice with PBS, the skins are cut into pieces (<1 mm×1 mm) using a surgical blade knife, and completely digested using I type collagenase (1 mg/ml). The supernatant is abandoned. The cells are resuspended through a complete medium and seeded to a culture dish. After 90% cells are fused, the cells are subcultured. Epithelium contamination may occur during the process of primary culture, and most of parenchyma cells (epithelial and endothelial cells) will die gradually after several subculture. Therefore, the cells used in embodiments of the present invention are cells that have been subcultured for more than three generations (cell culture and identification are as shown in FIG. 2).

Working Example 3

Culture of Skin Stem Cells and Directional Differentiation Toward Schwann Cells

Figure 3:
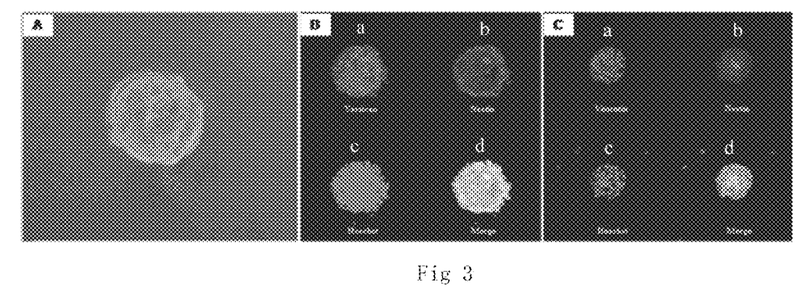

This is conducted as previously described (Jeffrey A Biernaskie, Ian A McKenzie, Jean G Toma & Freda D Miller, *Skin-derived precursors (SKPs) and differentiation and enrichment of their Schwann cell progeny NATURE PROTOCOLS*, 2006(1): 2803-2812). In brief, newborn SD rats (1 day old) are killed and disinfected with alcohol. Skins in the back are taken out and placed in a pre-cooled dissection solution to remove subcutaneous tissue (fat, hypodermic fascia layer, and blood vessels). After wash thrice with PBS, the skins are cut into pieces (<1 mm×1 mm) using a surgical blade knife, and completely digested 0.1% pancreatin or XI type collagenase (1 mg/ml) for 45-60 min at 37° C., and then the digestion is terminated via a complete medium. The centrifugation is conducted and the supernatant is abandoned. Suspension culture is conducted in DMEM/F12 (3:1) containing 0.1% secondary antibody, 40 μg/ml Fungizone (amphotericin B), 40 ng/ml FGF2, 20 ng/ml EGF, and 2% B27 supplement. The resultant cell spheres are subcultured to obtain a sufficient quantity of skin stem cells. The cell culture and identification are shown in FIG. 3).

Figure 4:
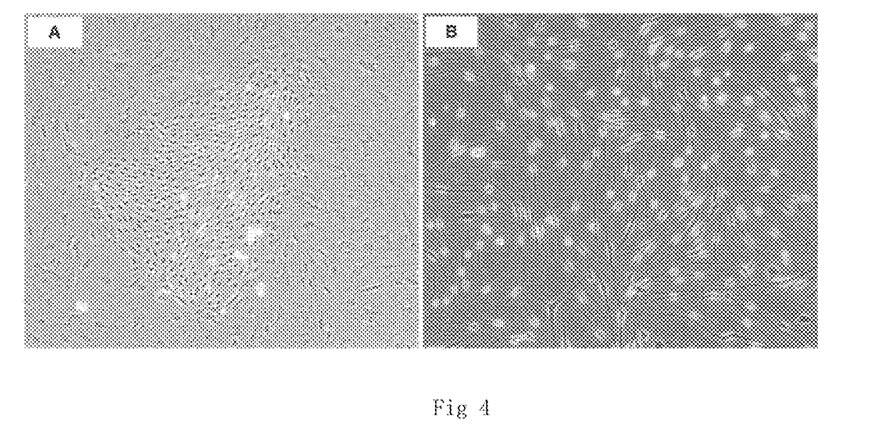
Figure 5:
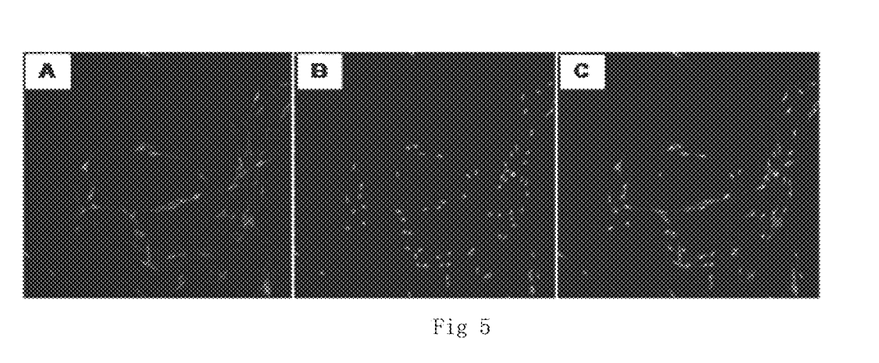

The obtained skin stem cells are differentiated toward the Schwann cells through the following steps. The skin stem cells are cultured in a differentiation medium I (DMEM/F12 (3:1) containing 0.1% secondary antibody, 40 μg/ml Fungizone (amphotericin B), 40 ng/ml FGF2, 20 ng/ml EGF, 2% B27 supplement and 10% FBS) for 3 d, and then are cultured in a differentiation medium II (DMEM/F 12_(3:1) containing 0.1% secondary antibody, 5 μm forskolin, 50 ng/ml heregulin-1β, 50 μg/ml, 2% N2supplement, and 1% FBS for two to three weeks, thus forming Schwann cell colony (FIG. 4.A). Schwann cells (SKP-SCs) differentiated by skin stem cells proliferate after colony amplification (FIG. 4.B). The immunohistochemistry results shows that the cells are immunopositive to S100 (FIG. 5).

Working Example 4

Culture of Bone Marrow Mesenchymal Stem Cells

Figure 6:
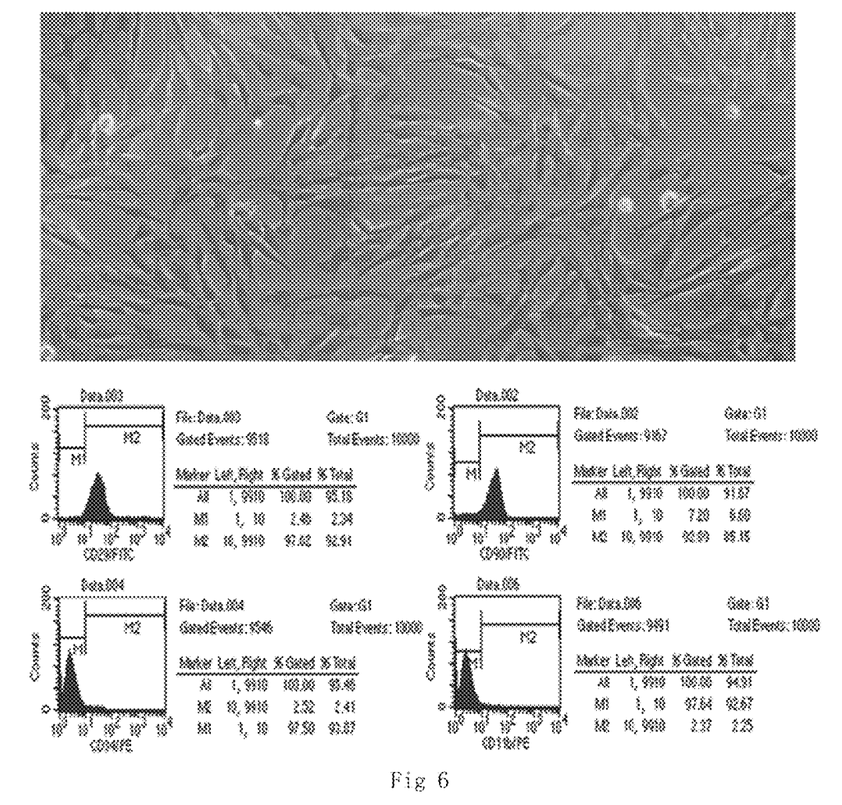
FIG. 6—Flow cytometry of bone marrow mesenchymal stem cells and Immunohistochemistry with CD molecules.

Adult SD rats are killed by dislocation, soaked for 5 min with 75% alcohol. Femur and fetal bone are taken at an aseptic condition, and the marrow cavities are exposed and flushed by IMDM basal culture solution to collect the bone marrow. The bone marrow obtained is repeatedly pumped with an injector and prepared into a single-cell suspension, which is filtered through a 200-mesh sieve, placed in a horizontal centrifuge for centrifugation (1000 rpm×5 min). After the supernatant is abandoned, The cells are seeded at a density of $4\times10^5/cm^2$ to an IMDM complete culture solution (containing 10% fetal calf serum) for culture. Full-dose solution change is conducted after 24 h, and the cells not adhered to the wall are removed. Afterwards, half-dose solution change is conducted every 3 d. The cell modality and growth situation are daily observed under an inverted microscope. When the cells overspread the bottom of the culture dish and are fused by 90%, the cells are subcultured (the cell culture and identification are shown in FIG. 6).

Working Example 5

Decellularization of Support Cells

Figure 7:
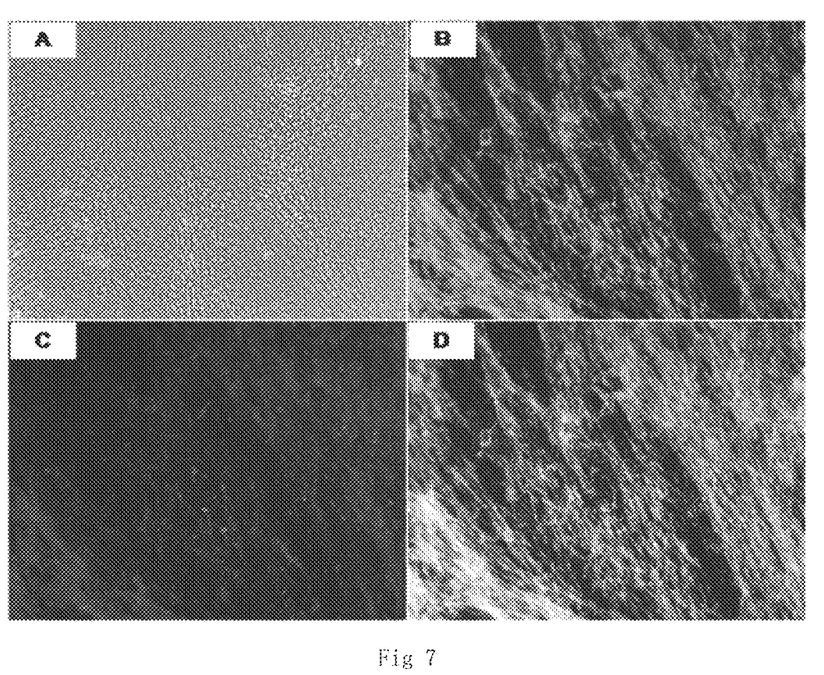

Support cells (for example, Schwann cells) are cultured in a culture dish. When the cells overspread the bottom of the culture dish and are fused by 90%, the cells are cultured for two weeks in a differentiation medium (H-DMEM+15% FBS+50 ng/ml HRG+2 μm forsklin+50 μg/ml Vc) to stimulate ECM secretion. After PBS wash, the cells are decellularized, and subjected to hypotonic treatment for 10 min in deionized sterile water at 37° C. The cell extracts (PBS containing 0.5% TritonX-100 and 20 mM aqueous ammonia) are added to crack the cells for 10-15 min at 37° C., and Dnase I (4 mg/ml) is added for digestion for 30 min at 37° C. to remove DNA. The obtained ECM is as shown in FIG. 7.A. Partial components of the ECM is identified by LN and FN immunochemistry. The ECM is fixed for 30 min at a room temperature with 4% paraformaldehyde, and to allow reaction with primary antibodies, i.e. mouse anti-laminin (LN) and rabbit anti-fibronectin (FN), respectively, overnight at 4° C., followed by incubation with secondary antibodies, i.e., FITC-conjugated goat anti-rabbit-IgG (1:200) and TRITC-conjugated goat anti-mouse-IgG (1:200), respectively, for 2 h at room temperature, and detection under confocal fluorescent microscopy (DMR, Leica) (FIGS. 7. B-D).

Working Example 6

Natural ECM Beneficial to Axonal Growth

Figure 8:
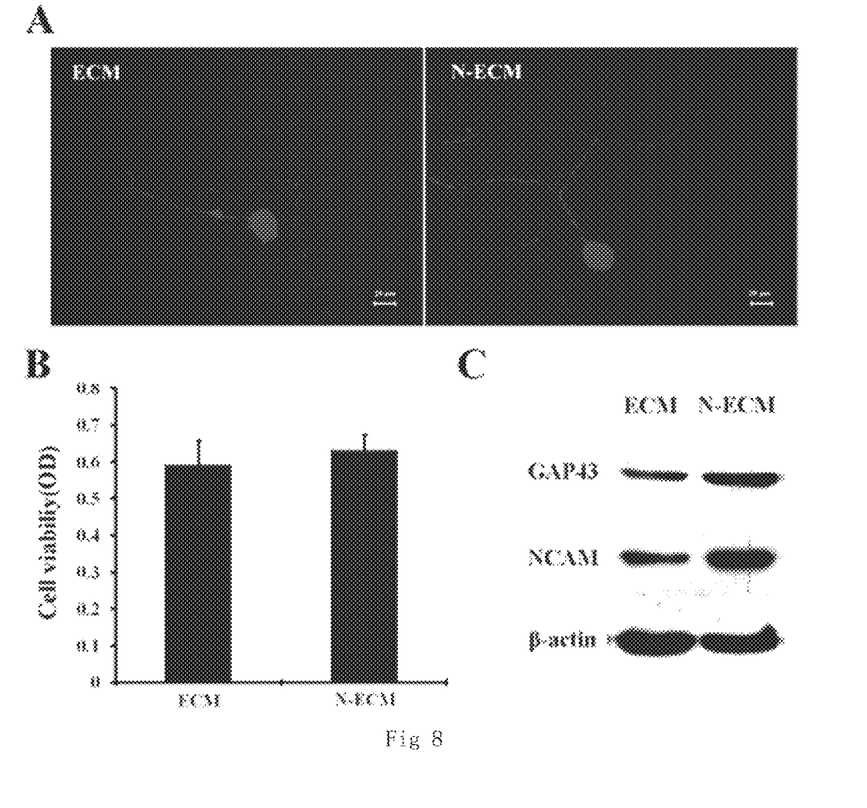

Dorsal root ganglion neurons are seeded into a culture disk of coated with ECM derived from acellular support cells, as obtained in Working example 5 or with commercially available ECM (SIGMA, goods No.: E0282) for 48 h culture, the cell vitality of neurons is detected by MTT method, while the axonal growth is observed by immunocytochemistry, and the expression of GAP43 and CAM) are detected by Western Blotting. The results are shown in FIG. 8. There is no statistics difference in the cell viability of the neurons on the two types of ECM. Immunocytochemistry results, however, displays that the neuron axon is obviously longer cultured on the acellular support cells-derived ECM than cultured on the purchased ECM, and Western Blotting displays that the expression of GAP43 or NCAM in the neurons cultured on the acellular support cells-derived ECM is higher than that of the neurons cultured on the purchased ECM, respectively (FIG. 8).

Working Example 7

Preparation of Support Cells-Containing Tissue Engineered Nerve Grafts

Chitosan nerve conduits and silk fibroin filaments are treated aseptically, 120 pieces of silk fibroin monofilaments are inserted into the lumen of a chitosan nerve conduit as luminal fillers to give a composite nerve conduit. A 100 ml complete medium (DMEM+10% FBS+50 ng/ml HRG+2 µM forsklin) is slowly put into a culture vessel through a peristaltic pump, and then $2.5 \times 10^7$ cells and a sterile nerve conduit are added, followed by processing with a peristaltic pump to ensure the final cell density of $1 \times 10^5$/ml. After air is exhausted from the culture vessel, a rotational microgravity circulation perfusion culture is initiated with a rotational bioreactor placed in a 37° C. $CO_2$ incubator to ensure a full contact and adhesion of cells onto the nerve conduit by setting the rotating speed of 10 r/min at the first 24 h, and then to make the nerve conduit suspended in a culture solution by adjusting the rotating speed after 24 h. Following culture for 2 d, the medium is changed with a differentiation medium (H-DMEM+15% FBS+50 ng/ml HRG+2 µm forsklin+50 µg/ml Vc) every 3 d to promote ECM secretion, and allowed to culture for two more weeks before the support cells-coated nerve conduit is taken out, which is the resultant tissue engineered nerve graft.

Figure 9:
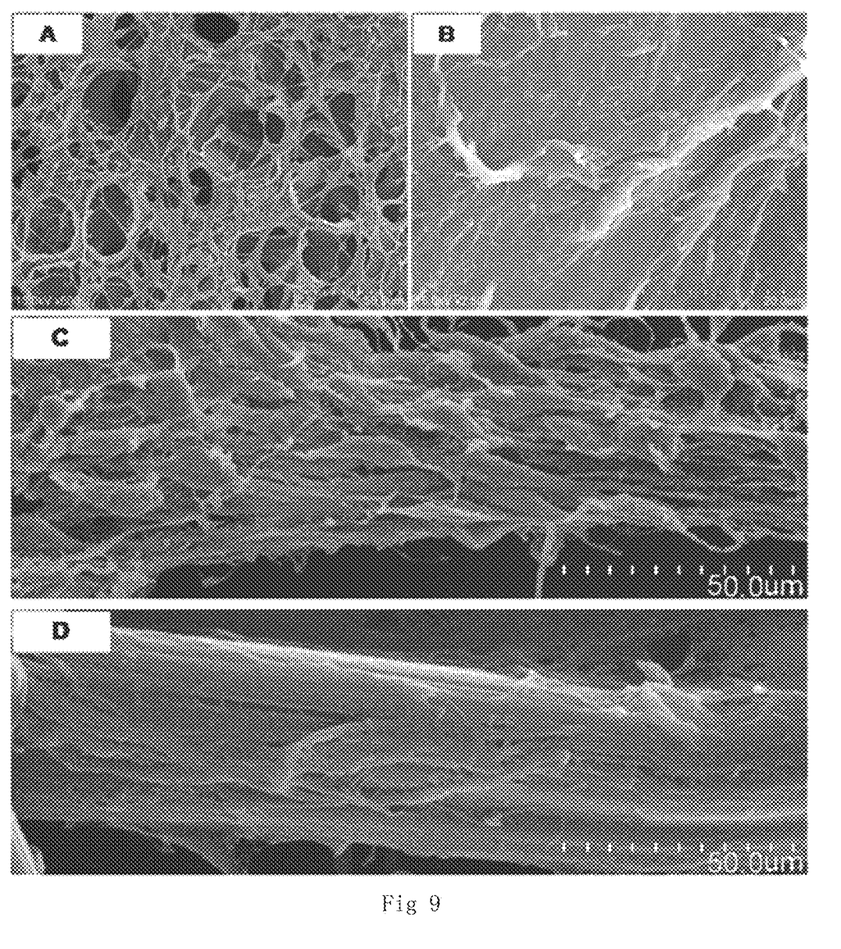

SEM displays that support cells are uniformly distributed on both the surface of the nerve conduit and the silk fibroin filaments (FIGS. 9A and 9C). To perform SEM observation, the resultant tissue engineered nerve graft is fixed with 4% glutaric acid at 4° C., washed thrice with PBS, fixed with 1% osmic acid at room temperature for 2 h, washed twice with PBS, dehydrated in graded concentrations (30, 50, 70, 80, 95 and 100%) of ethanol for 10 min respectively, and then incubated by changing the medium with a mixture of ethyl alcohol and tertiary butyl alcohol (1:1), and pure tertiary butyl alcohol for 10 min each time. After lyophilization and platinum spray, the sample is observed under a scanning electron microscope (TCS SP2, Leica).

Working Example 8

Construction of Support Cells-Derived ECM Modified Tissue Engineered Nerve Grafts The support cells-containing tissue engineered nerve grafts, as prepared in Working example 7, are subjected to decellularization. It is washed with PBS, placed in sterile deionized water at 37° C. for hypotonic treatment, followed by cell lysis in a nonionic detergent (consisting of 0.5% TritonX-100 and 20 mM aqueous ammonia) for 10-15 min at 37° C., and in a nonionic detergent plus Dnase I (4 mg/ml) for 30 min digestion at 37° C. to remove DNA.

Figure 10:
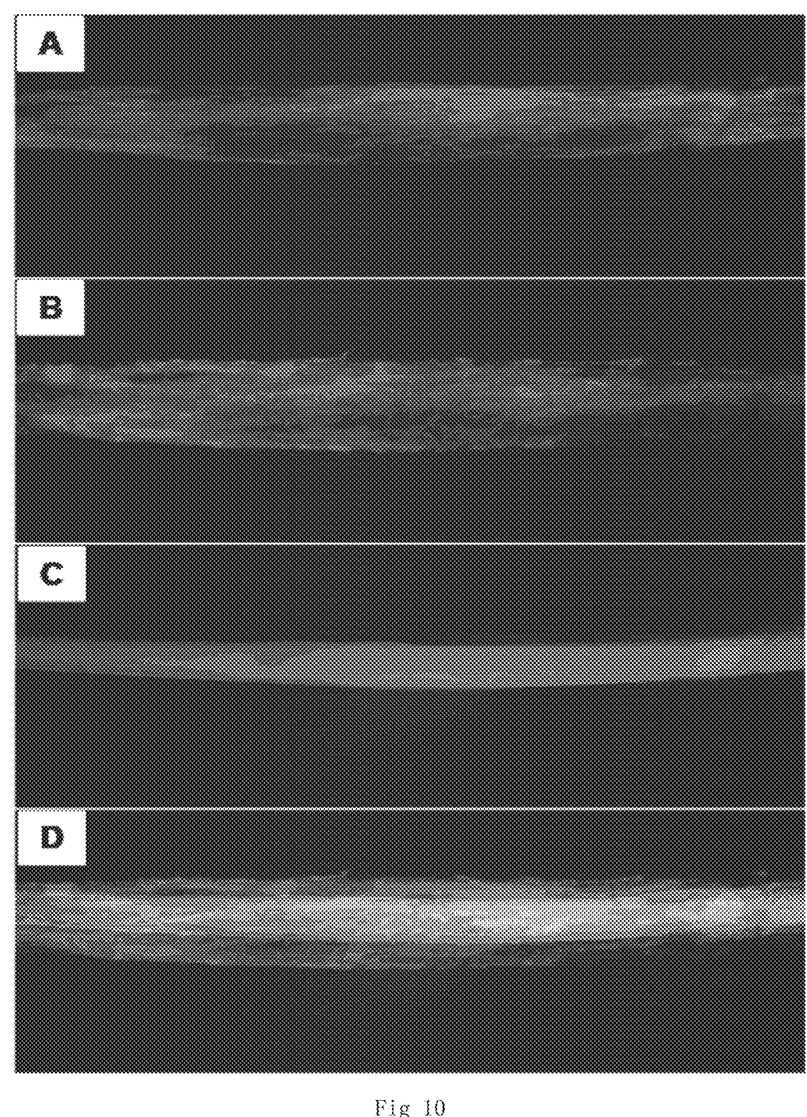
Figure 11:
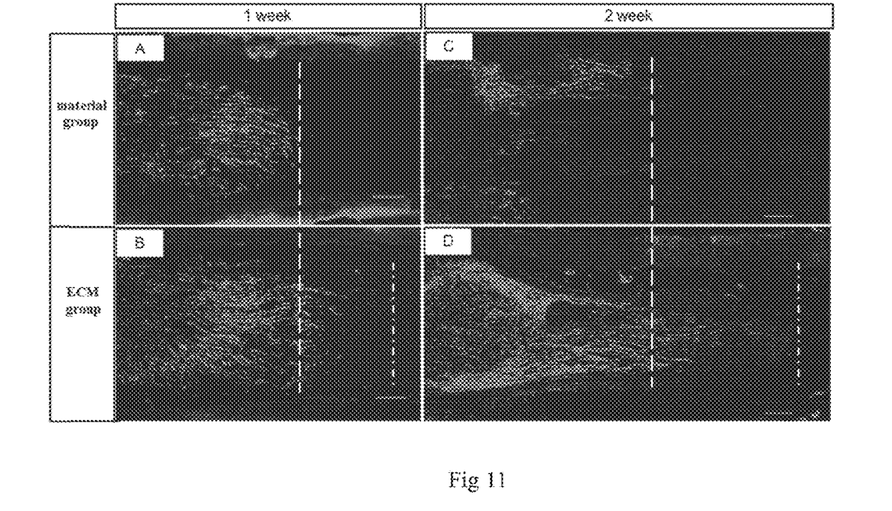

SEM displays that the support cells-derived ECM components are uniformly distributed on both the surface of the nerve conduit and the silk fibroin filaments (see FIGS. 9B and 9D). The prepared ECM modified tissue engineered nerve graft is saved at −80° C. for use. The reserved ECM components after decellularization are respectively observed under SEM and detected by immunochemistry, in which SEM detection is the same as that in example 7, and an immunochemistry method is the same as that in example 5. The results are shown in FIG. 10.

Working Example 9

Repairing Sciatic Nerve Defects of Rats by Cell-Derived ECM Modified Tissue Engineered Nerve Grafts The rat sciatic nerve defects are repaired by cell-derived ECM modified tissue engineered nerve grafts, and nerve regeneration and function restoration are detected using by a series methods, such as immunohistochemistry, transmission electron microscopy (TEM), electrophysiology, morphological evaluation of target muscles.

Figure 12:
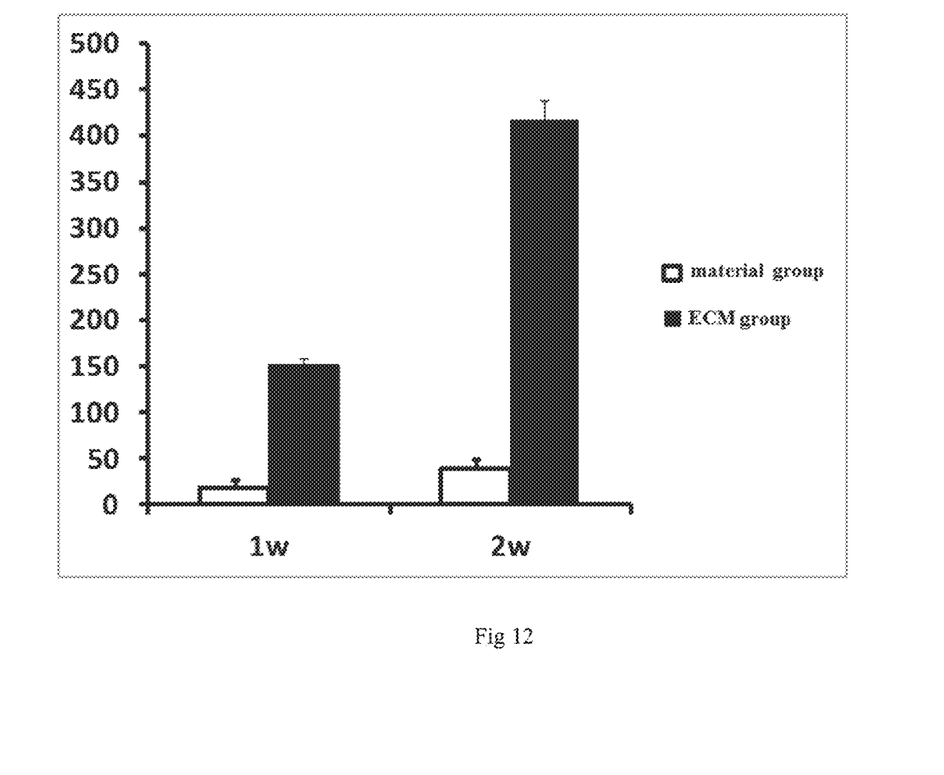
FIG. 12 Histogram for statistical comparisons for regenerated nerve fibers among the indicated groups.
Figure 13:
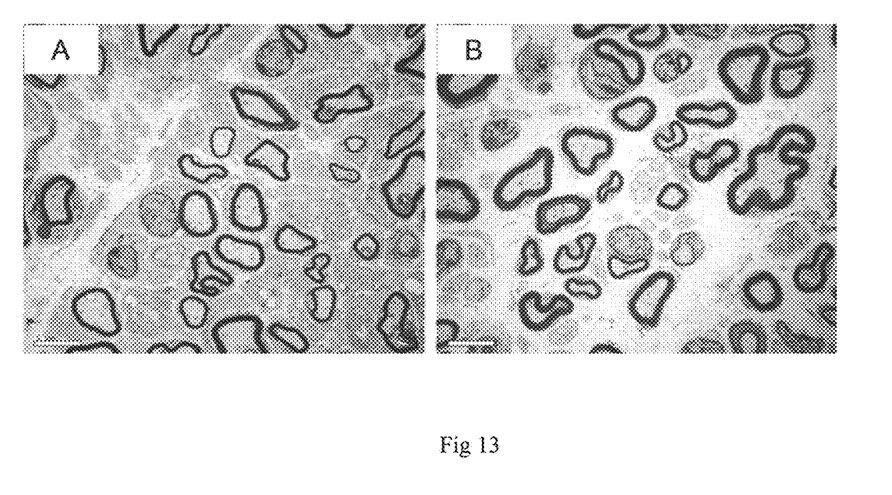

The rat sciatic nerve injury model with a 10 mm-long defect is established. The animals are randomly divided into two groups: one group is using cell-derived ECM modified tissue engineered nerve grafts for repairing the sciatic nerve defects of rats, called a ECM group, and another group is using plain tissue engineered nerve grafts (without ECM modification) for repairing the sciatic nerve defects of rats, called a material group. At one or two weeks post surgery, animals are transcardially perfused, and the regenerated nerve segments are then harvested and cut into sections. NF immunohistochemistry shows that the nerve growth in ECM group is faster than that of material group. NF positive nerve fibers in ECM group are relatively dense and distributed more uniformly (FIG. 11A-D), and statistical comparisons are shown in FIG. 12. The sciatic nerves of all the animals are exposed under proper anaesthesia at three months post-surgery, and electrophysiological detection is conducted. The mean compound muscle action potential (CMAP) amplitude is 4.63±0.13 mV and 6.89±2.85 mV in material group and ECM group respectively, and there is a significant difference (P<0.05) between two groups. TEM shows that at three months post surgery, some of the regenerated mylinated nerve fibers are dispersedly distributed in the middle portion with less unmylinated nerve fibers in two groups (FIGS. 13A and B). The thicknesse of the nerve myelin sheath are respectively is 0.63±0.27 µm, and 0.82±0.39 µm in material group and ECM group respectively, and there is a significant difference (P<0.05) between two groups.

The invention claimed is:

1. A method of preparing a tissue engineered nerve graft for repairing a peripheral nerve defect including a nerve conduit and an ECM, being prepared with a three-dimensional microgravity rotational culture to generate a support cells-containing nerve graft and then obtaining an autologous or allogeneic cell-derived ECM-modified nerve graft via decellularization, the method comprising the steps of:
 preparing the nerve conduit by electrostatically spinning a biodegradable material selected from the group consisting of silk fibroin, chitosan and a combination thereof;
 preparing the support cells-containing nerve graft, wherein a complete medium is added to a culture vessel, and then $2.5 \times 10^7$ cells selected from the group consisting of Schwann cells, skin-derived fibroblasts, skin stem cells, bone marrow mesenchymal stem cells, induced pluripotent stem cells and a combination thereof and the nerve conduit are added to the culture vessel;

processing with a peristaltic pump to ensure a final cell density of $1\times10^5$/ml, after air is exhausted from the culture vessel;

initiating a rotational microgravity circulation perfusion culture with a rotational bioreactor placed in a 37° C. $CO_2$ incubator to ensure a full contact and adhesion of the cells onto the nerve conduit by setting a rotating speed of 10 r/min at the first 24 h, and then suspending the nerve conduit in a culture solution comprising Iscove's Modified Dulbecco's Media (IMDM) by adjusting the rotating speed after 24 h, further wherein following culture for 2 d, the medium is changed with a differentiation medium to promote ECM secretion, and allowed to culture for two more weeks before the nerve conduit, now coated with support cells is taken out; and constructing a decellularized tissue engineered nerve graft, wherein the support cell-containing tissue engineered nerve graft is subjected to decellularization, and is washed with phosphate buffered saline, placed in sterile deionized water at 37° C. for hypotonic treatment for 10 min, followed by cell lysis in a nonionic detergent for 10-15 min at 37° C., and adding of DNAse I at a concentration of 4 mg/ml to the nonionic detergent at 37° C. to remove DNA, and the acellular product is kept at −80° C. for use.

2. The method according to claim 1, further comprising the step of uniformly distributing the ECM on an inner and an outer surface of the nerve conduit, the ECM comprising a combination of collagen, laminin, fibronectin, hyaluronic acid and proteoglycan.

3. The method of claim 1, wherein the tissue engineered nerve is composed of a nerve conduit comprising chitosan chitosan, and the nerve conduit has a porosity of 50-90%, a pore size of 50-300 μm, an inside diameter of 0.5-8 mm and a wall thickness of 0.1-3 mm.

4. The method of claim 1, wherein the nerve conduit is a silk fibroin-based nanoscale nerve conduit.

5. The method of claim 1, wherein the complete medium is a mixture of heregulin-1β (HRG), forskolin, Dulbecco's modified Eagle's medium (DMEM) and fetal bovine serum (FBS).

6. The method of claim 1, wherein the differentiation medium is a mixture comprising:

HEPES buffered Dulbecco's modified Eagle's medium (H-DMEM), HRG, FBS and forskolin, a mixture comprising DMEM, amphotericin B, fibroblast growth factor-2 (FGF-2), epidermal growth factor (EGF), a B27 supplement and FBS or a mixture comprising DMEM, HRG, forskolin and an N-2 supplement.

7. A tissue engineered nerve graft for repairing a peripheral nerve defect including a nerve conduit and an ECM, prepared according to the method of claim 1.

8. A method of preparing a tissue engineered nerve graft for repairing a peripheral nerve defect comprising the steps of:

preparing a nerve conduit by electrostatically spinning silk fibroin and a biodegradable material selected from the group consisting of chitosan, collagen, polylactic acid, polyglycolic acid and a combination thereof;

preparing a support cell-containing nerve graft by adding a complete medium to a culture vessel, and then adding the nerve conduit and $2.5\times10^7$ cells selected from the group consisting of Schwann cells, skin-derived fibroblasts, skin stem cells, bone marrow mesenchymal stem cells, induced pluripotent stem cells and a combination thereof to the culture vessel;

processing contents of the culture vessel with a peristaltic pump to ensure a final cell density of $1\times10^5$/ml, after air is exhausted from the culture vessel;

initiating a rotational microgravity circulation perfusion culture with a rotational bioreactor placed in a 37° C. $CO_2$ incubator to ensure a full contact and adhesion of the cells onto the nerve conduit by setting a rotating speed of 10 r/min at the first 24 h, and then suspending the nerve conduit in a culture solution comprising Iscove's Modified Dulbecco's Media (IMDM) by adjusting the rotating speed after 24 hours, further wherein following culture for 2 days, the complete medium is changed with a differentiation medium to promote ECM secretion, and allowed to culture for two more weeks before the nerve conduit, now coated with support cells is taken out; and constructing a decellularized tissue engineered nerve graft, wherein the support cell-containing tissue engineered nerve graft is subjected to decellularization, and is washed with phosphate buffered saline, placed in sterile deionized water at 37° C. for hypotonic treatment for 10 min, followed by cell lysis in a nonionic detergent for 10-15 min at 37° C., and adding of DNAse I at a concentration of 4 mg/ml to the nonionic detergent at 37° C. to remove DNA, and the acellular product is kept at −80° C. for use.

9. The method according to claim 8, further comprising the step of uniformly distributing the ECM on an inner and an outer surface of the nerve conduit, the ECM comprising a combination of collagen, laminin, fibronectin, hyaluronic acid and proteoglycan.

10. The method of claim 8, wherein the tissue engineered nerve is composed of a nerve conduit comprising chitosan and the nerve conduit has a porosity of 50-90%, a pore size of 50-300 μm, an inside diameter of 0.5-8 mm and a wall thickness of 0.1-3 mm.

11. The method of claim 8, wherein the nerve conduit is a silk fibroin-based nanoscale nerve conduit.

12. The method of claim 8, wherein the complete medium is a mixture comprising heregulin-1β (HRG), forskolin, Dulbecco's modified Eagle's medium (DMEM) and fetal bovine serum (FBS).

13. The method of claim 8, wherein the differentiation medium is a mixture comprising:

HEPES buffered Dulbecco's modified Eagle's medium (H-DMEM), HRG, FBS and forskolin, a mixture comprising DMEM, amphotericin B, fibroblast growth factor-2 (FGF-2), epidermal growth factor (EGF), a B27 supplement and FBS or a mixture comprising DMEM, HRG, forskolin and an N-2 supplement.

14. A tissue engineered nerve graft for repairing a peripheral nerve defect including a nerve conduit and an ECM, prepared according to the method of claim 8.

* * * * *

UNITED STATES PATENT AND TRADEMARK OFFICE
CERTIFICATE OF CORRECTION

PATENT NO. : 9,492,589 B2
APPLICATION NO. : 14/762243
DATED : November 15, 2016
INVENTOR(S) : Xiaosong Gu It is certified that error appears in the above-identified patent and that said Letters Patent is hereby corrected as shown below:

On the Title Page

Abstract (Line 2), please change
"and a" to --and an--

Abstract (Line 7), please change
"a EMC" to --an EMC--

In the Specification

Column 1, Line 20, please change
"repair" to --repair.--

Column 1, Line 36, please change
"can" to --can- --

Column 2, Line 61, please change
"and a" to --and an--

Column 3, Line 1, please change
"of of" to --of--

Column 3, Line 39, please change
"nerve nerve" to --nerve--

Column 3, Line 42, please change
"nerve nerve" to --nerve--

Signed and Sealed this
Eleventh Day of April, 2017

Michelle K. Lee
*Director of the United States Patent and Trademark Office*

CERTIFICATE OF CORRECTION (continued)
U.S. Pat. No. 9,492,589 B2

Column 4, Line 49, please change
"than an" to --than a--

Column 8, Line 4, please change
"shows" to --show--

Column 8, Line 64, please change
"of coated" to --coated--

Column 10, Line 28, please change
"a ECM" to --an ECM--

Column 10, Line 48, please change
"thicknesse" to --thickness--

In the Claims

Column 11, Line 37 (Claim 3, Line 3), please change
"chitosan, and" to --and--